(12) United States Patent
Salacz

(10) Patent No.: US 6,811,239 B1
(45) Date of Patent: Nov. 2, 2004

(54) METHOD OF INKJET PRINTING IN HIGH EFFICIENCY PRODUCTION OF HYGIENIC ARTICLES

(75) Inventor: Philipp Oskar Imre Salacz, Baden-Würtemberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/441,522

(22) Filed: May 20, 2003

(51) Int. Cl.[7] .............................. B41J 29/38; B41J 2/01; A61F 13/15; A61F 13/20; B41F 17/00
(52) U.S. Cl. .............................. 347/12; 347/104; 347/2; 604/361; 101/44
(58) Field of Search .............................. 347/8, 9, 2, 104, 347/106, 107, 12; 242/615.12, 615.21; 604/361, 358; 355/24; 101/36, 37, 38.1, 39, 40, 40.1, 41, 42, 43, 44

(56) References Cited

U.S. PATENT DOCUMENTS

| 4,909,879 | A | | 3/1990 | Ball |
|---|---|---|---|---|
| 5,458,590 | A | | 10/1995 | Schleinz |
| 5,682,183 | A | | 10/1997 | Wade |
| 5,699,090 | A | | 12/1997 | Wade |
| 6,120,142 | A | * | 9/2000 | Eltgen et al. ............... 347/104 |

FOREIGN PATENT DOCUMENTS

| EP | 0 603 748 A1 | 6/1994 |
|---|---|---|
| EP | 0 843 037 A2 | 5/1998 |
| EP | 1 295 711 A1 | 3/2003 |

* cited by examiner

Primary Examiner—Michael S Ball
Assistant Examiner—Alfred Dudding
(74) Attorney, Agent, or Firm—Michael S. Kolodesh

(57) ABSTRACT

Disclosed is a method of inkjet printing of tone and/or color images at a high efficiency production of hygienic articles. The method provides a reliable system of combining inkjet-printing operations with converting operations on a converting line producing hygienic articles having tone and/or color print images. The method utilizes at least two-inkjet print heads capable of switching between the print heads during malfunctions or maintenance procedures of one of the print heads to provide production continuity at a minimum production loss of hygienic articles.

10 Claims, 9 Drawing Sheets

METHOD OF INKJET PRINTING IN HIGH EFFICIENCY PRODUCTION OF HYGIENIC ARTICLES

FIELD OF THE INVENTION

This invention relates to a method of inkjet printing in high-efficiency production of hygienic article having print images.

BACKGROUND OF THE INVENTION

Hygienic articles, such as disposable absorbent articles, including feminine hygiene articles, baby diapers, baby pull-on articles, adult incontinence articles, and the like, including images printed on inner and/or outer surfaces thereof have been disclosed in a copending, commonly assigned U.S. application Ser. No. 10/025,059, filed on Dec. 19, 2001, which is hereby incorporated herein by reference.

The print images can be single-tone, multi-tone, single-color, or multi-color. These images should be visible to the consumer in order to provide the consumer with a variety of desired benefits including improved aesthetics, product functional benefits, or consumer awareness of how good the product is. For example, a two-tone image, shown in FIGS. 1–3, emits a perception of depth, which can be important for the consumer expecting satisfactory liquid absorption and retention capabilities from the product. The perception of depth indicates that although the product is thin, the performance of the product will not be compromised by the thinness.

The print images are generally provided by printing ink on substrate materials by various printing methods, such as flexographic printing, rotogravure printing, screen-printing, inkjet printing, and the like. Typically, the printing operations are accomplished on high-speed printing lines, separately from the converting lines that are dedicated to manufacturing disposable absorbent articles. After printing on the printing lines, the printed substrates are delivered to the converting lines, typically in a form of continuous webs comprising printed images thereon. However, the above practice of separately printing the substrates off the converting lines typically requires additional cost associated with handling, winding and unwinding, storing and shipping of the substrates. In addition, the above steps can negatively affect the quality of the printed substrate, resulting in uneven and often excessive deformations of the wound layers of the substrate inside the roll due to uneven distribution of the compression forces inside the roll. Furthermore, the separately printed substrates often require special registration control methods to ensure proper phasing of the printed images with the converting operations to effect a desired and consistent positioning of the printed image in the produced article.

However, combining the printing operations with converting operations on the converting lines producing disposable absorbent articles at a high-speeds and a high production efficiency can result in substantial production losses, as overall efficiency of the converting line is often compromised. This is due generally to the multiplicity and complexity of the converting operations, wherein any malfunction of any of the converting operations can affect the performance of the printing operation, and vice versa, any malfunction of the printing operation can affect the converting operations. In addition, the printing operations often require periodic maintenance procedures that can also affect the production efficiency of the converting lines. Because converting lines can be high-speed operations, producing hundreds or thousands of hygienic articles per minute, any interruption of the production process can result in substantial production losses.

Therefore, it would be beneficial to provide a reliable method of combining printing operations with converting operations on a converting line for high-efficiency production of hygienic articles having print images.

SUMMARY OF THE INVENTION

The present invention can provide a method of inkjet printing in a high efficiency production of hygienic articles, having print images, on a converting line including at least two inkjet print heads. The method includes the steps:

(a) providing a substrate moving in the web direction at a first velocity;

(b) printing on the substrate a first plurality of images by a first inkjet print head disposed in proximity to the substrate, the images are separated from each other in the web direction at a pitch interval;

(c) switching from the first inkjet print head to a second inkjet print head while the substrate continues its movement; and (d) printing on the substrate a second plurality of images by a second inkjet print head disposed in proximity to the substrate, the images are separated from each other at the pitch interval, wherein the first plurality of images is separated from the second plurality of images by an unprinted region in the web direction, wherein the unprinted region is no greater than 50 times the pitch interval.

In another aspect of the invention, the unprinted region is no greater than 10 times of the pitch interval. In yet another aspect of the invention, the unprinted region is no greater that 1 time of the pitch interval.

In one aspect of the invention, the step of switching from the first inkjet print head to a second inkjet print head can include the following steps:

(a) initiating a second start signal by an operator to a converter controller for starting the second inkjet print head;

(b) ceasing sending a first output signal from the converter controller to the inkjet controller; and (c) sending a second output signal from the converter controller to the inkjet controller.

In another aspect of the invention, the step of switching from the first inkjet print head to a second inkjet print head can include the following steps:

(a) ceasing sending a first OK signal from the inkjet controller responding to a fail mode of the first inkjet print head;

(b) ceasing sending a first output signal from the converter controller to the inkjet controller, and (c) starting sending a second output signal from the converter controller to the inkjet controller.

In one aspect of the invention, the high efficiency production of hygienic articles, having print images, on a converting line including at least two inkjet print heads is at least 60% efficiency. In another aspect of the invention, the high efficiency production of hygienic articles, having printed images, on a converting line including at least two inkjet print heads is at least 70% efficiency. In yet another aspect of the invention, the high efficiency production of hygienic articles, having print images, on a converting line including at least two inkjet print heads is at least 85% efficiency.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
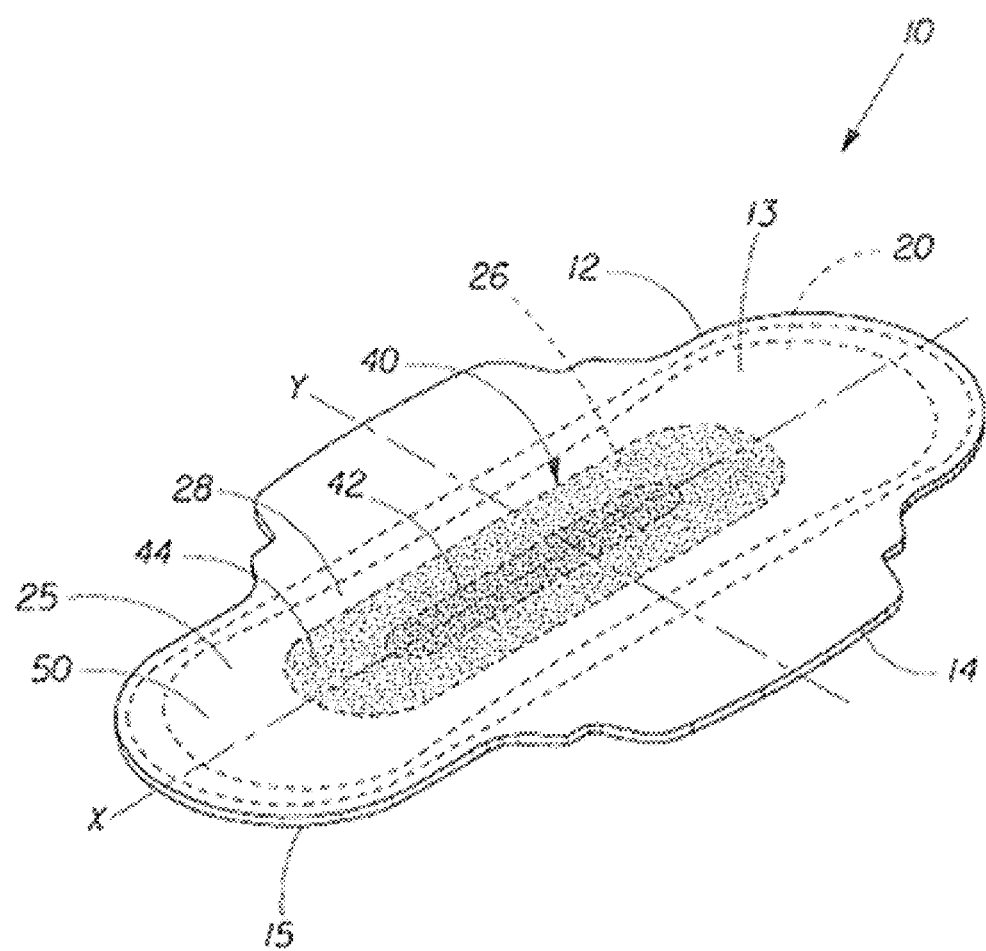
FIG. 1 is a perspective view of an exemplary hygienic article having a print image.

The present invention will be described with respect to a disposable absorbent article, having a multi-tone signal of at least one color printed on a topsheet surface of the absorbent article, disclosed in a copending and commonly assigned U.S. patent application Ser. No. 10/025,059, filed Dec. 19, 2001. Specifically, the present invention will be described with respect to a feminine hygiene article disclosed in the above patent application. However, the present invention can be applicable to any disposable absorbent article having single-color and/or multi-color and/or single-tone and/or multi-tone images printed on the outer and/or inner surfaces to provide a variety of desired benefits including improved product performance, product aesthetics, consumer awareness, consumer perception, and the like.

Definitions

The term "hygienic article," "disposable absorbent article," or "absorbent article" refers herein to a device that normally absorbs and retains fluids. In certain instances, the phrase refers to devices that are placed against or in proximity to the body of the wearer to absorb and contain the excreta and/or exudates discharged from the body, and includes such personal care articles as feminine hygiene articles, baby diapers, baby pull-on articles, baby swim articles, adult incontinence articles, and the like. In other instances, the phrase refers to protective articles, such as, for example, dining bibs that have the ability to absorb food items to prevent staining of the wearer's clothing. In still other instances, the phrase refers to devices providing some therapeutic benefit, such as, for example, pain relief, wound coverage or to hold another device or article near the body.

The term "disposable" is used herein to describe products which generally are not intended to be laundered or otherwise restored or extensively reused in their original function, i.e., preferably they are intended to be discarded after several uses or after a single use.

The term "substrate" is meant herein any material, preferably in a form of a continuous web, suitable for printing an image on at least one of the opposite surfaces thereof. The term "substrate" can include a film (breathable or non-breathable), a non-woven material, a woven material, a foam material, or any combination thereof. The substrate can be a single layer or multiple layers, comprising synthetic and/or natural materials. The substrate can also include a dry lap material including wood pulp, and the like, having a single layer or multiple layers. Furthermore, the substrate can be part of any component of a hygienic article, such as, for example, a topsheet, a secondary topsheet, an insert, a backsheet, an absorbent core, or any combination thereof.

The term "color" as referred to herein includes any primary color, i.e., white, black, rod, blue, violet, orange, yellow, green, and indigo as well as any declination thereof or mixture thereof. The term 'non-color' or 'non-colored' refers to the color white which is further defined as those colors having an L* value of at least 90, an a* value equal to 0±2, and a b* value equal to 0±2. The color scale values utilized herein can be made with a Hunter Color reflectance meter, a description of which can be found in an article by R. S. Hunter, 'Photoelectric color difference Meter', Journal of the Optical Society of America, Vol. 48, pp.985–95, 1958. Devices specially designed for the measurement of color on the Hunter scales are described in U.S. Pat. No. 3,003,388 to Hunter et al., issued Oct. 10, 1961.

The term "feminine hygiene article" refers herein to sanitary napkins, panty liners, tampons, and incontinence articles worn by women to absorb and contain menses as well as other vaginal and incontinent exudates. Non-limiting examples of feminine hygiene articles that can be provided with a multi-tone signal that operates to create depth perception include those manufactured by The Procter & Gamble Company of Cincinnati, Ohio as: ALWAYS® Pantiliners with DriWeave® manufactured according to U.S. Pat. Nos. 4,324,246; 4,463,045; and 6,004,893; ALWAYS® Ultrathin Slender Maxi with Wings manufactured according to U. S. Pat. Nos. 4,342,314, 4,463,045, 4,556,146, B1 4,589,876, 4,687,478, 4,950,264, 5,009,653, 5,267,992, and Re. 32,649; ALWAYS® Regular Maxi; ALWAYS® Ultra Maxi with Wings; ALWAYS® Maxi with Wings; ALWAYS® Ultra Long Maxi with Wings; ALWAYS® Long Super Maxi with Wings; and ALWAYS® Overnight Maxi with Wings, each aforesaid publication being incorporated by reference herein.

The term "pitched unit operation" refers herein to any device on a converting line, having a pitch-related function for working one or more webs in the manufacture of disposable absorbent articles. For example, the unit operation can include, but is not limited to such pitched-related web-working devices as a cutting device (e.g., a final knife), a discrete patch placing device (e.g., a cut-and-slip unit, a cut and placement unit), an embossing device having a pitched embossing pattern, a web activator device (e.g., incremental-stretch activation devices disclosed in U.S. Pat. No. 5,151,092 to Buell et al.; U.S. Pat. No. 5,156,793 to Buell et al., and U.S. Pat. No. 5,518,801 to Chappell et al.), a rotary printing device, and the like, all of which have in common that they include a manufacturing cycle corresponding to a product pitch length, which is the length of the product in a web form on a converting line before the web is cut into individual products.

The term "efficiency" or "reliability" of a production operation refers herein to a ratio, expressed in percents, of a production output produced during a period of seven (7) consecutive working days, 24 hours per day, to a theoretical production output that could have been produced if there were no production outages of any of the unit operations of the converting line due to malfunctions, maintenance, and the like.

The term "high efficiency production" referrers herein to the efficiency or reliability of a converting line producing hygienic articles, wherein the efficiency of the converting line is at least 60%, at least 70%, or at least 85%. The efficiency of the converting line depends on the efficiency of each unit operation of the converting line. For example, the efficiency of the printing operation of the present invention is about 99.7%.

DESCRIPTION

Figure 2:
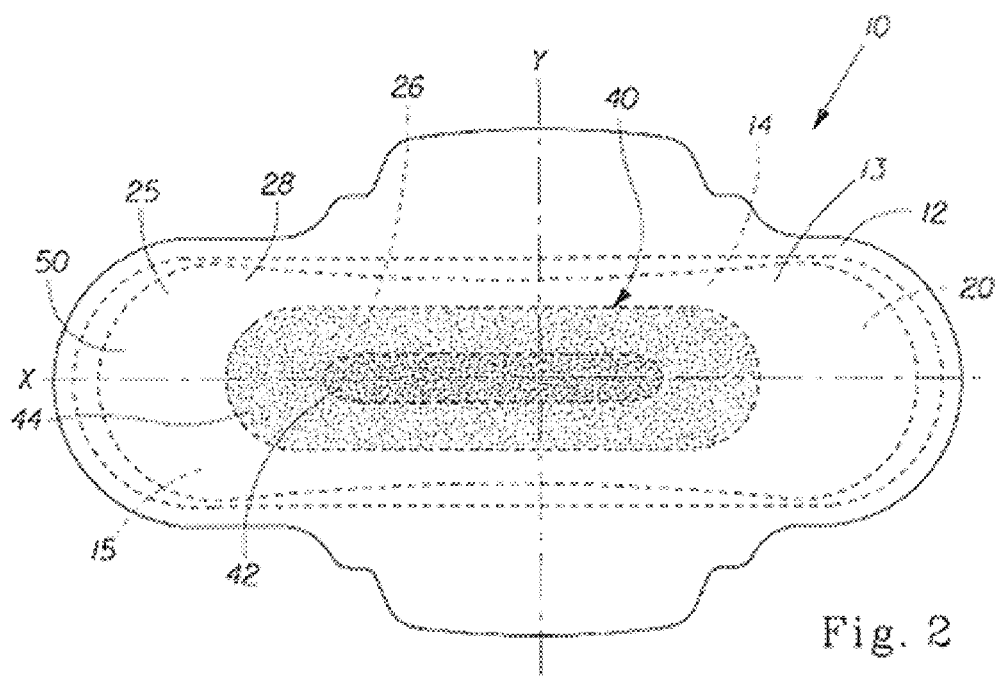
FIG. 2 is a plan view of the hygienic article of FIG. 1.

FIG. 1 provides a perspective view of an absorbent article 10, which is presented herein in a form of a feminine hygiene article. FIG. 2 provides a plan view of the absorbent article 10 of FIG. 1. The absorbent article 10 herein has an upper surface or user facing surface 13, a lower surface or garment facing surface 14, and a periphery 12. The absorbent article 10 comprises a topsheet 25 having a viewing surface 28 facing upwardly towards the upper surface 13. The absorbent article 10 further comprises a backsheet 15 positioned oppositely to the topsheet 25. The backsheet 15 is joined to the topsheet 25 preferably at least partially at the periphery 12. The absorbent article 10 also comprises an absorbent core 20 positioned between the topsheet 25 and the backsheet 15. In a preferred embodiment of the present invention, the absorbent article 10 also includes a secondary topsheet or an insert 26 positioned beneath the topsheet 25, i.e., at least partially, between the topsheet 25 and the absorbent core 20.

In the embodiment shown in FIG. 1 and in FIG. 2, the absorbent article 10 has at least two portions, i.e., a colored portion 40 and a non-colored portion 50. The colored portion 40 and the non-colored portion 50 are viewable from the viewing surface 28 of the topsheet 25. The colored portion 40, which in a preferred embodiment of the present invention is a print image 40, has at least two shades: a first shade 42 and a second shade 44. Preferably, but not necessarily, and as is shown in FIGS. 1 and 2, the first shade 42 is positioned substantially within the second shade 44. The second shade 44 is different, either in lightness, darkness, and/or color, from the first shade 42. The multi-shades operate to create a perception of depth within the absorbent article by a user looking upon the viewing surface 28 of the topsheet 25. In the embodiment shown in FIGS. 1 and 2, the first shade 42 of the print image 40 is darker than the second shade 44 of the print image 40.

Figure 3:
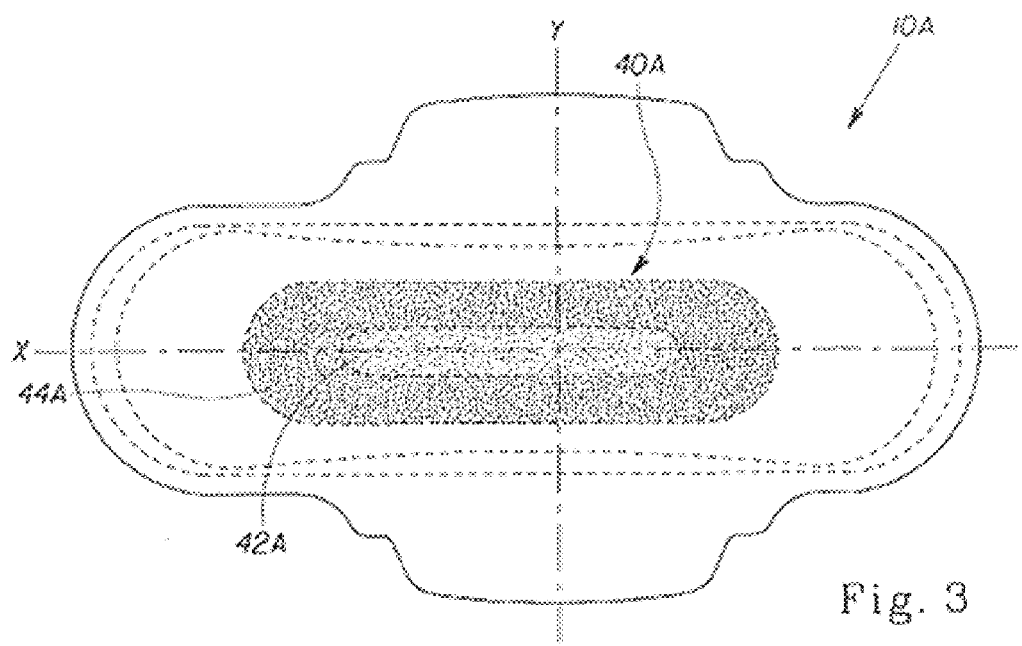
FIG. 3 is a plan view of an alternative embodiment of a hygienic article.

Alternatively, in another embodiment of the absorbent article 10A, a print image or a colored portion 40A can comprise a first shade 42A that is lighter than a second shade 44A, as shown in FIG. 3. The lightness and darkness of the shades, whether two or greater than two shades, are configured to create a perception of depth by a user looking upon the viewing surface 28 of the absorbent article 10A.

As described above, in one embodiment of the present invention, the print image 40 can be the secondary topsheet or an insert 26 positioned between the topsheet 25 and the absorbent core 20. In another embodiment, the colored portion 40 can form a part of the topsheet 25. In yet another embodiment, the print image 40 can form a part of the absorbent core 20 whereby the print image 40 is viewable from the viewing surface 28 of the topsheet 25. Alternatively, the printimage 40 can be a multi-layer insert positioned beneath the topsheet 28.

Any topsheet material that allows the print image 40 to be readily seen from the viewing surface 28 of the topsheet 25 is suitable. For example, formed film materials, nonwoven materials, or combinations thereof are suitable.

Figure 4:
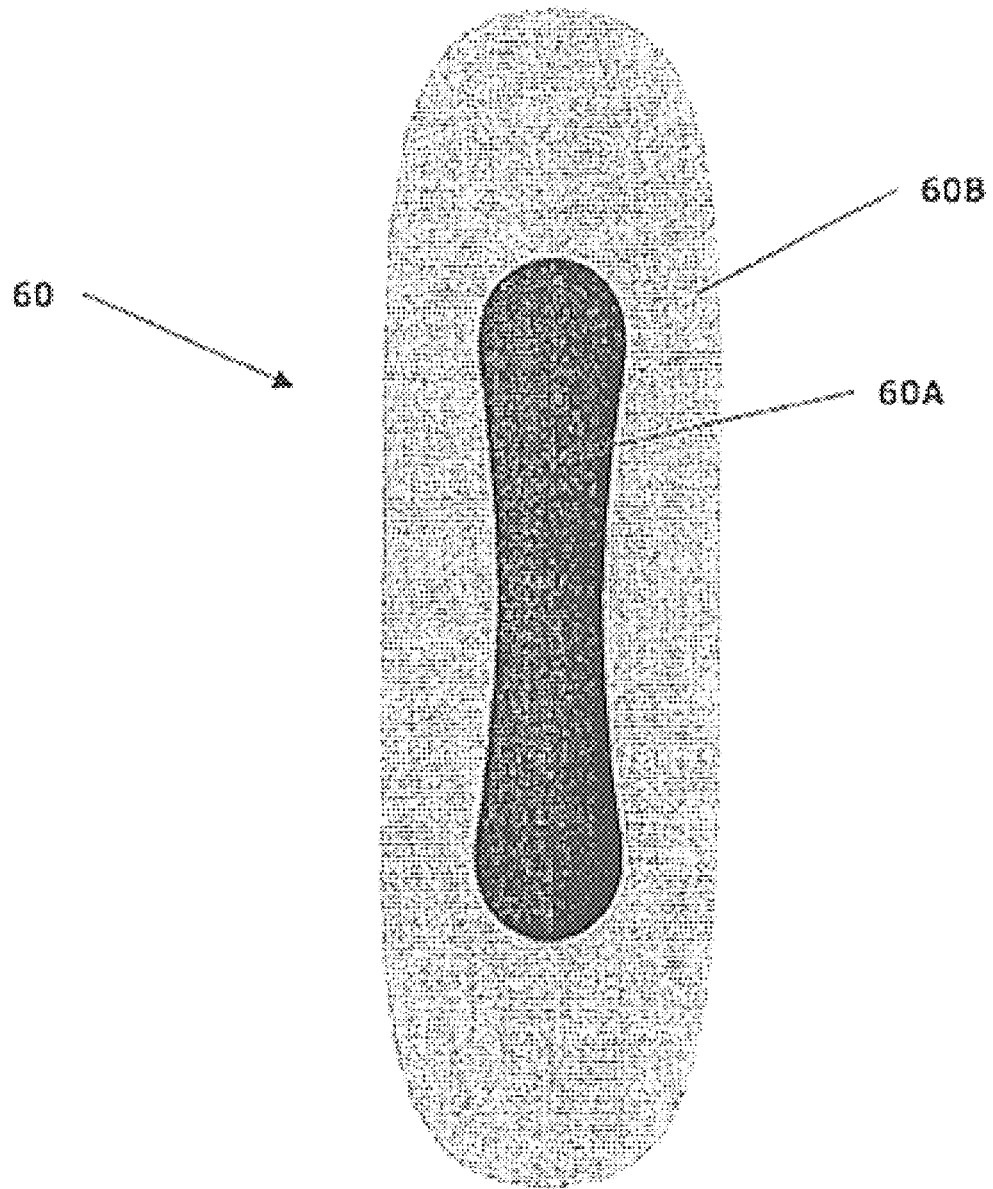
FIG. 4 is an exemplary two-tone image shown as a gray scale image.

Alternatively to the color scale values described above, the two-tone portions 40 and 40A can be shown as gray scale images. For example, FIG. 4 illustrates a two-tone image 60 having a darker portion 60A and a lighter portion 60B. The two-tone gray scale images of the present invention were measured using Adobe Illustrator® available from Adobe Systems Incorporated, the headquarters of which is located in San Jose, Calif. In one embodiment, the darker portion 60A was measured 45 on a gray scale and a lighter portion 60B was measured 20 on a gray scale.

Figures 5, 6:
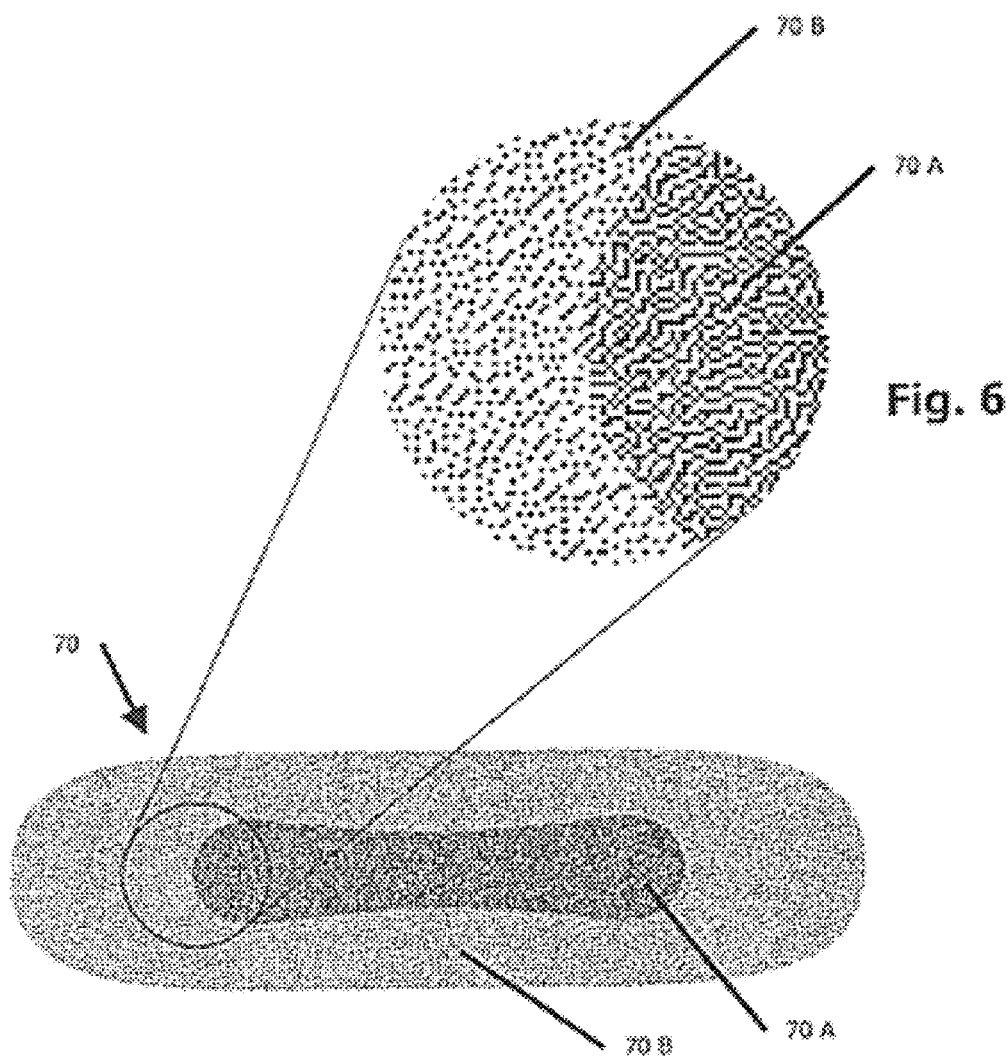
FIG. 5 is the two-tone image of FIG. 4 shown as a pcx image.
FIG. 6 is a magnification of a portion of the pcx image of FIG. 5.
Figure 7:
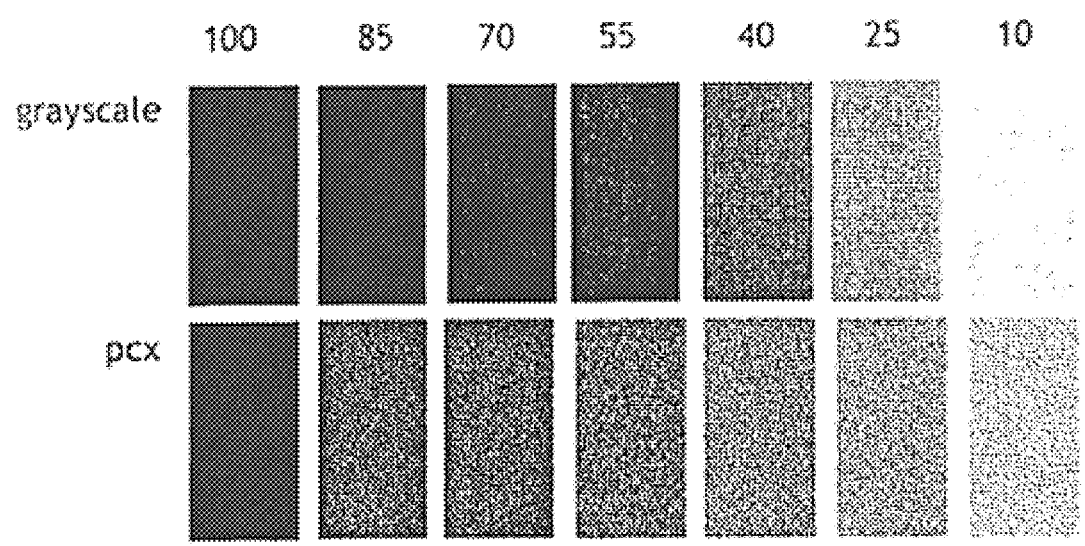
FIG. 7 illustrates a side-by-side comparison of various gray scale and pcx scale images.

A gray scale image can be converted into a pcx image by using Adobe Photoshop® also available from Adobe Systems Incorporated. FIG. 5 shows an image 70 as a pcx image converted from the gray scale image 60 of FIG. 4. Because a pcx image is comprised of individual pixels and dots, the pcx image can be useful in creating inkjet images, wherein each dot of a pcx image represents an ink dot formed by an inkjet of a print head. FIG. 6 shows a magnified view of the image 70, wherein the darker portion 70A is composed of a greater number of dots than the lighter portion 70B. For the reference purposes, FIG. 7 illustrates a side-by-side comparison of several gray scale images having gray scale values of 10, 25, 40, 55, 70, 85, and 100 to the corresponding pcx images, where the gray scale value of a 100 represents a completely black image.

Figure 8:
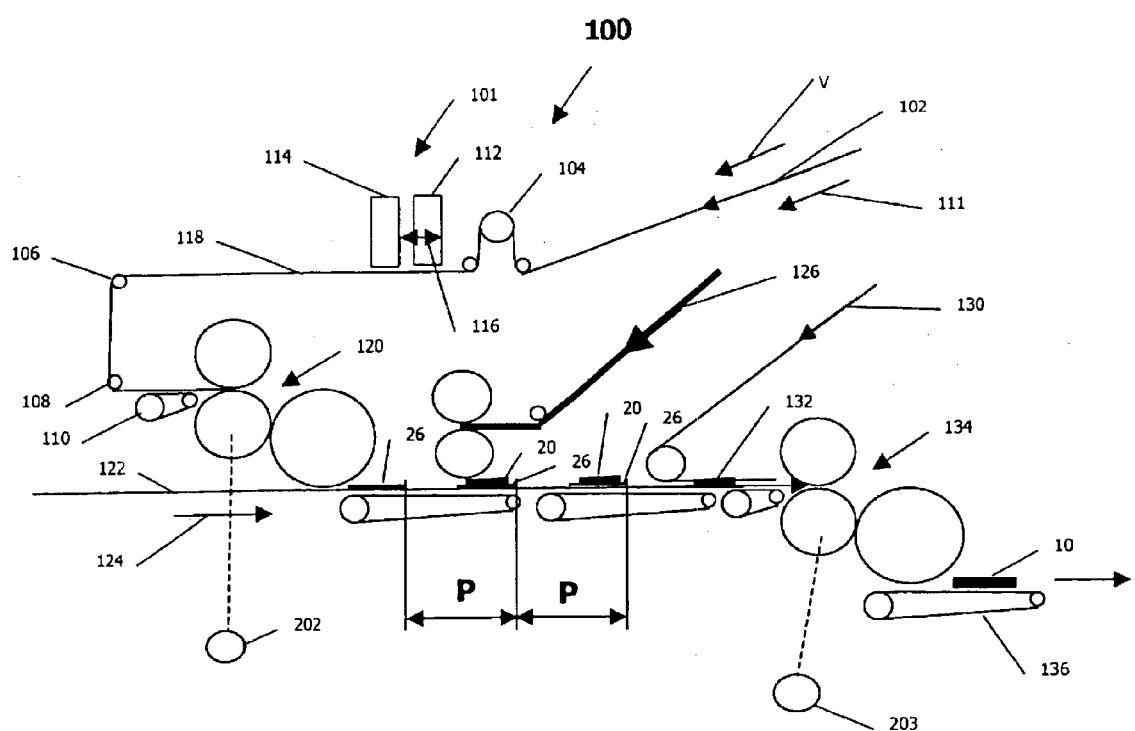
FIG. 8 is a simplified elevation view of one embodiment of the method of the present invention designed to manufacture the hygienic articles of FIGS. 1, 2 and 3, as well as any other hygienic article defined herein.

FIG. 8 is a simplified elevation view of one embodiment of a method 100 of the present invention designed to manufacture the absorbent articles of FIGS. 1, 2 and 3, as well as any other absorbent articles defined above and having any desired print image, including multi-colored, multi-tone, or multi-gray images.

The method 100 includes an inkjet printing station 101 capable of printing a desired image on a substrate 102. The substrate 102 can be any substrate according to the definition of a substrate provided above. Also, as described above, the substrate 102 can form any component or part of a disposable absorbent article 10. However, in the preferred embodiment of the present invention, the substrate 102 is a nonwoven web for use as the secondary topsheet or the insert 26, as shown in FIGS. 1 and 2.

The substrate 102 can be provided to the printing station 101 by any suitable means, such as, for example a metering device 104 (e.g., an omega roll or an s-wrap device), a series of idle rollers 106 and 108, and a metering device 110 (e.g., a vacuum conveyor). Both the metering devices 104 and 110 create a desired tension in the substrate 102 and move the substrate 102 in a web or machine direction 111 at a desired linear velocity V, which in the high-speed production method of the present invention can be as high as about 6 meters/second or even greater. However, the present invention is applicable at any other linear velocity V of the substrate, such as, for example, at least 5 meters/second, at least 4 meters/second, at least 3 meters/second, at least 2 meters/second, and lower (which occurs during a startup of the converting line when the converting line speed, including the linear velocity V of the substrate 102, is gradually increasing from a zero to a desired production speed).

As shown in FIG. 8, the printing station 101 preferably includes a dual-head arrangement comprising a first inkjet print head 112 and a second inkjet print head 114, disposed at a spatial distance 116 extending in the web direction 111. However, it should be noted that the first and the second print heads 112 and 114 could be disposed from each other at any desired spatial distance.

The first and the second print heads 112 and 114 can be any type that is suitable to print a desired image, and are preferably non-contact inkjet print heads disposed at a certain suitable distance from the substrate 102, i.e., from the first surface 118 of the substrate 102, facing the print heads 112 and 114.

The print heads 112 and 114 can be preferably supplied by ink provided by a common ink source; although if desired, separate ink sources can be also utilized.

Each of the print heads 112 and 114 includes a multiplicity of jets dispensing a multiplicity of substantially uniform ink dots. In one embodiment of the present invention, each of the print heads 112 and 114 includes 256 jets, forming a linear configuration of about 2 inches long (about 50.8 mm). Therefore, each of the print heads 112 and 114 can print an ink image containing 256 ink dots extending linearly about 50.8 mm across the substrate 102. This arrangement is sufficient for printing any image of up to about 50.8 mm wide, as measured across the substrate 102 and shown as a width W of the printed images 40 and 40A in FIGS. 1–2 and 3, respectively. However, any number of jets per a print head can be provided, if desired, to print a desired width W of a desired image, which, for example, for feminine hygienic articles of the present invention can vary from 5 mm to 85 mm. For other types of hygienic articles listed above, the width W of the print image can vary even greater.

With respect to the print heads having 256 jets, such print heads are available from Videojet Technologies, Inc., which offices are located in Wood Dale, Ill. The printing station 101 can be a part of an inkjet printing system that is also available from Videojet Technologies, Inc., as the PrintPro™ inkjet print system including an ink source and a controller for providing ink and controlling jets forming individual ink droplets.

In the PrintPro™ inkjet print system, the ink droplets are dispensed from all of the jets of the print heads 112 and 114 continuously, but only certain ink droplets are allowed to reach the substrate 102 at desired locations to form a printed image. The other ink droplets can be prevented from reaching the substrate 102 by deflecting the ink droplets into a recycling flow for a continuous re-use. The operation of the individual ink jets of each print head can be controlled by a controller included in the PrintPro™ system.

Alternatively to the continuous type of the inkjet printing system of one embodiment of the present invention, the inkjet printing system can be an on-demand type inkjet printing system, wherein ink typically is not recycled, and wherein ink droplets are not formed continuously, but on the demand basis, in a desired order, to print a desired image.

Referring again to FIG. 8, in the method of the present invention, each of the first and the second print heads 112 and 114 is capable of printing the images 40 and 40A of FIGS. 1–2, and 3, or any other desired image, separately from each other. For example, when the first print head 112 is in a print mode (i.e., is printing the image 40 on the substrate 102 at a desired location on the substrate 102), the second print head 114 can be in a standby or idle mode (i.e., is not printing the image 40 on the substrate 102). Conversely, when the first print head 112 is in a standby mode, the second print head 114 is in a print mode, printing the image 40. As described above, in both modes of operation, the print mode and the standby mode, the droplet formation by each of the 256 jets of each of the print heads 112 and 114 occurs continuously; however, in the standby mode, all of the dispensed droplets are deflected and recycled into a recycled ink flow, but in the print mode the un-deflected droplets are deposited on the substrate 102 and the deflected droplets are recycled into the recycle ink flow.

In the method of the present invention, by switching from the print mode of the first print head 112 to the print mode of the second print head 114, and vice versa, a desired continuity of the production process can be provided. The switching between the print heads 112 and 114 enables continuous, uninterrupted production of hygienic articles on a converting line when a print head needs to be taken out of the print mode for any reason, including any type of malfunction or scheduled maintenance, for cleaning and the like. The second print head provides a desired back up by automatically switching from a standby mode to a production mode.

This continuity is important to maintain a high production efficiency of a converting line producing hygienic articles at high production speeds, which, as described above, can be as high as 6 meters/second and greater, and at high production rates, which can be at least 600 products/minute, in order to avoid production losses, which, at such high speeds and production rates, can be substantial. (It should be noted that the method of the present invention is also applicable to any production rate, lower or greater of at least 600 products/minute, as high as 3,000 products per minute.)

It is important for the disposable absorbent articles of the present invention, to have a print image disposed at a desired, predetermined, and consistent location of hygienic articles. Therefore, in the method of the present invention, when the first print head 112 stops printing and the second print 114 starts printing, the second print head 114 can print in the identical location as did the first print head 112. Further, in one embodiment of the present invention, the switching between the print heads occurs simultaneously, with preferably a minimum loss of production of hygienic articles during the switching. This operation will be described in more detail below.

Referring again to FIG. 8, after the inkjet printing, the substrate 102 travels to a cut and placement device 120, capable of severing the substrate 102 into individual sheets comprising the secondary topsheet 26 and then placing the secondary topsheets 26 at a desired pitch interval P onto a topsheet web 122 moving in a web direction 124 at a desired velocity. The topsheet web 122 can be provided and metered at a desired velocity by any suitable means known to one skilled in the art. Then, an absorbent core web 126 (which can be also provided and metered by any suitable means) is cut into individual absorbent cores 20, which are then placed onto the secondary topsheet 26, previously disposed on the topsheet web 122. The cutting and placing operations of the absorbent core 20 can be provided by a cut-and-slip device 128 or any suitable web cutting and placing device known in the art. Further, a backsheet web 130 (which can be also provided and metered by any suitable means) is deposited onto the cores 20 to provide a sandwiched-type web 132, which is subsequently bonded together and cut into individual hygienic articles 10 of the present invention. The bonding, cutting, and placing operations of the sandwiched-type web 132 can also be provided by any suitable means known in the art, for example, by a final knife 134. The individual articles 10 then can be transported by any suitable means, such as a conveyor 136, to other downstream operations, such as folding, wrapping, and packing.

Figure 9:
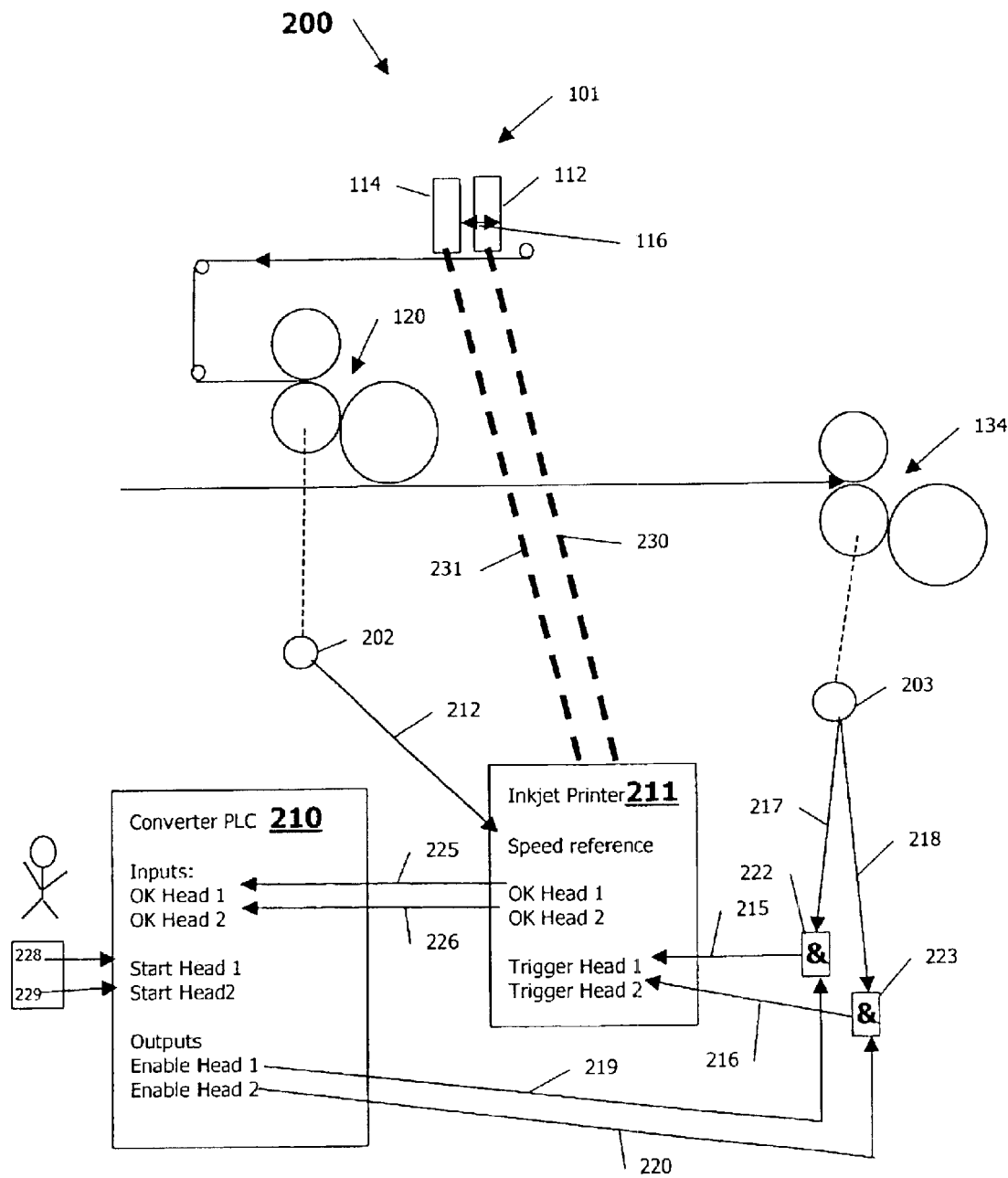
FIG. 9 is a block diagram of one embodiment of the control system of the method of present invention.

FIG. 9 illustrates a block diagram 200 of one embodiment of the control system of the present invention. The diagram 200 includes the printing station 101 having the first inkjet print head 112 and the second inkjet print head 114. The block diagram 200 also includes an inkjet controller 211 for calculating the deflection of each ink droplet of each of the 256 nozzles of each of the print heads 112 and 114. The calculated information is then transferred from the inkjet controller 211 to the inkjet print heads 112 and 114, using a first communication link 230 and a second communication link 231, respectively. The inkjet controller 211 also receives information from a first encoder 202 with respect to a converter speed reference (e.g., a linear velocity of the moving substrate 102), which can be provided from any suitable speed reference representing the speed of the substrate 102. In one embodiment of the present invention, the speed reference 212 is provided from the cut and placement device 120 via the first encoder 202 connected to the cut and placement device 120. The inkjet controller 211 further receives triggering information with respect to the print heads 112 and 114, wherein each print head 112 and 114 has its own triggering signal, i.e., a first triggering signal 215 and a second triggering signal 216, respectively.

With respect to controlling the first print head 112, as shown in FIG. 9, the first triggering signal 215 is a result of information calculated by a first calculation unit 222 receiving a first start cycle signal 217 and a first output signal 219. The first calculation unit 222 can be any suitable electronic device capable of calculating a binary AND logic function, for example, an opto-couple device and the like. The first start cycle signal 217 is provided by a second encoder 203, which in the preferred embodiment of the present invention, is connected to the final knife 134. However, the second encoder 203 can be connected to any pitched unit operation defined above, including the cut and placement device 120 that can be attached to both the first encoder 202 and the second encoder 203. The first output signal 219 is provided from a converter logic controller 210 (referred hereinafter as a converter controller 210). In order to provide the first output signal 219, the converter controller 210 receives both a first OK signal 225 and a second OK signal 226 from the inkjet controller 211.

Similarly, with respect to controlling the second print head 112, as shown in FIG. 9, the second triggering signal 216 is a result of information calculated by a second calculation unit 223 receiving a second start signal 218 and a second output signal 220. The second calculation unit 223, similarly to the first calculation unit 222, can be any suitable electronic device capable of calculating a binary AND logic function. The second start cycle signal 218 is provided by the second encoder 203. The second output signal 220 is provided from the converter controller 210. In order to provide the second output signal 220, the converter controller 210 receives both the first OK signal 225 and the second OK signal 226 from the inkjet controller 211.

The first start cycle signal 217 and the second start cycle signal 218 are related to each other, representing the spatial distance 116 between the respective nozzles of the first and the second print heads 112 and 114. The spatial distance 116 presents a portion of a single product cycle corresponding to a cycle distance between the first and the second print heads 112 and 114.

Figure 10:
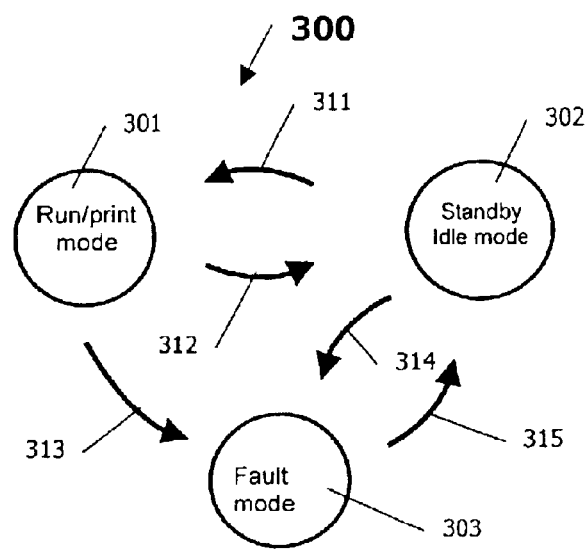
FIG. 10 is a block diagram of a switching logic between the operating modes of the inkjet print heads according to the method of the present invention.

FIG. 10 shows a block diagram 300 illustrating logic for switching between three operating modes of the first and the second inkjet print heads 112 and 114, within the converter controller 210. The three operating modes of each of the print heads 112 and 114 are illustrated by three circles representing a standby or idle mode 301, a run mode 302, and a fault mode 303.

In the standby mode 301, the first print head 112 or the second print head 114 (or both print heads 112 and 114) are ready for printing at any moment, while continuously forming and re-circulating ink droplets into a recycled ink flow.

In the run mode 302, the first print head 112 or the second print head 114 prints an image on the substrate 102. (As noted above, in a preferred embodiment of the present invention, only one of the print heads 112 or 114 can operate in the run mode 302 at the time.) In both the standby mode 301 and the run mode 302, the converter controller 210 receives the OK signal 215 or 216 and sends the output signal 219 or 220 (see FIG. 9).

In the fault mode 303, the converter controller 210 does not receive the OK signal 215 or 216 and does not send the output signal 219 or 220 (see FIG. 9).

Referring to FIG. 10, from the standby mode 301, a print head can switch to the run mode 302 by a transition 311 or to the fault mode 303 by a transition 314. The transition 311 can happen as a consequence of two different situations: (1) an operator switching between print heads by initiating start signals 228 or 229 (see FIG. 9) for the first print head 112 or the second print head 114, respectively, to the converter controller 210; or (2) the transition 311 is an automated sequence happening immediately after a transition 313 on the other print head, which switched from the run mode 302 to the fault mode 303. With respect to the transition 314, it can also happen as a consequence of two different situations: (1) an operator switching an idling print head to the fault mode 303 when the idling print head needs maintenance, such as cleaning and the like; or (2) an idling print head failing for any reason, and, accordingly, not sending the OK signal 225 or 226 to the converter controller 210.

Referring to FIG. 10, from the run mode 302, a print head can switch to the standby mode 301 by a transition 312, or to the fault mode by a transition 313. The transitions 312 and 313 are equal in priority, and, therefore, each one becomes executed depending upon which of the transitions 312 or 313 occurs first. The transition 312 can happen when an operator switches between the print heads, and the transition 313 can happen when a print head fails in the run mode 302 (i.e., does not send the OK signal 225 or 226 to the converter controller 210) and needs operator service. When a print head fails in the run mode 302, the other, idling print head, switches to the run mode 302 by the transition 311.

Referring to FIG. 10, from the fault mode 303, a print head can switch only to the standby mode 301 by the transition 315. This happens after a faulted print head has been serviced and is ready for operation.

Operating Procedures

Referring again to FIGS. 9 and 10, below are described various procedures for continuous operation of the first and the second print heads 112 and 114.

At the start, the first and the second print heads 112 and 114 are preferably in the standby mode 301 controlled by the converter PLC 210. When both print heads 112 and 114 are in the standby mode 301, the inkjet controller 211 sends both OK signals 225 and 226 to the converter controller 210. Now the operator has an option to select either one of the print heads 112 or 114 to start printing by initiating the first start signal 228 for starting the first print head 112 or the second start signal 229 for starting the second print head 114. If the operator selects to start the first print head 112 by initiating the first start signal 228, the converter controller 210 sends the first output signal 219, which is combined with the first cycle start signal 217 in the first calculation unit 222 sending the first triggering signal 215 to the inkjet controller 211 for starting the first print head 112. During the printing by the first print head 112 in the run mode 302, the second print head 114 remains in the standby mode 301, ready to be switched to the run mode 302 when needed. When the first print head 112 is printing in the run mode 302 and the second head 114 is in the standby mode 301, the inkjet controller 211 is sending both the first and the second OK signal to the converter controller 210.

When the first print head 112, becomes faulted, the inkjet controller 211 switches the first print head 112 to the fault mode 303 and stops sending the first OK signal 225 to the converter controller 211, which in response, stops sending the first output signal 219 and starts sending the second output signal 220. The second output signal 220 is then combined with the second start cycle signal 219 in the second calculation unit 223 sending the second triggering signal 216 to the inkjet controller 211 switching the second print head 114 to the run mode 302.

Similarly, when the second print head 114, becomes faulted, the inkjet controller 211 switches the second print head 114 to the fault mode 303 and stops sending the first OK signal 225 to the converter controller 211, which in response, stops sending the first output signal 220 and starts sending the first output signal 219. The first output signal 219 is then combined with the first start cycle signal 218 in the first calculation unit 222 sending the first triggering signal 215 to the inkjet controller 211 switching the first print head 112 to the run mode 302.

Alternatively to the automatic switching between the print heads described above when one of the print heads becomes faulted, the operator can switch between the print heads any time when the converter PLC is receiving both OK signals 225 and 226. For example, when the first print head 112 is working in the run mode 302 and the second print head 114 is in the standby mode 301 (in such condition, the converter PLC is receiving both OK signals 225 and 226 from the inkjet controller 210), and the operator can switch the printing from the first head 112 to the second print head 114 at any time by initiating the second start signal 229. In this case, the converter PLC stops sending the first output signal 219 and starts sending the second output signal 220, which is then combined with the second start cycle signal 219 in the second calculation unit 223 sending the second triggering signal 216 to the inkjet controller 211 switching the second print head 114 to the run mode 302. When the converter PLC 210 stops sending the first output signal 219 above, in response, the inkjet controller 210 stops receiving the first triggering signal 215 and stops sending the first OK signal 225 to the converter PLC 210. This manual switching between the print heads by the operator may be needed when the operator needs to do any service procedure (e.g., cleaning and the like) to a print head working in the run mode 302. Also, the operator may need to switch print head when there is a need to change the printing image by loading a new data. Such capability enables the operator to change a printing image "on the fly" without interrupting the production process on the converter.

Figure 11:
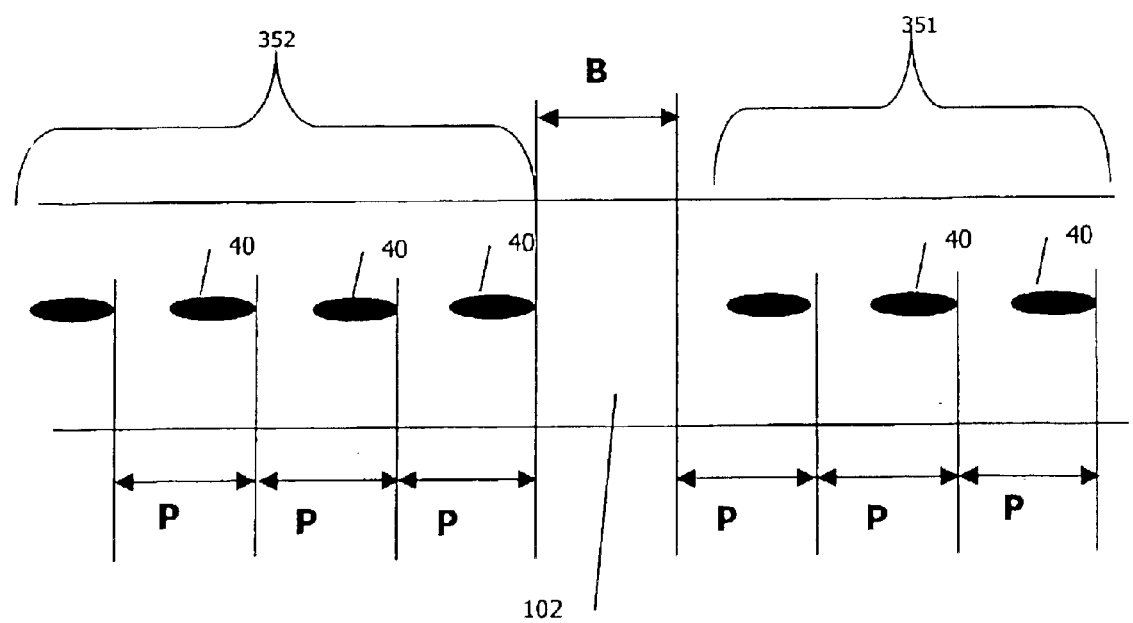
FIG. 11 is a top view of a portion of a substrate having a first plurality of images and a second plurality of images separated by an unprinted region B from the first plurality of images.

FIG. 11 shows a top view of a portion of the substrate 102 having a first plurality 351 of images 40 and a second plurality 352 of images 40. In the first plurality 351 of images 40 and in the second plurality 352 of images 40, the images 40 are separated from each other at a pitch interval P, which is the length of a hygienic article. The pitch interval P can very depending on a particular hygienic article, for example, generally from about 100 mm to about 400 mm. Specifically, with respect to feminine hygienic articles, the pitch interval P can vary from about 220 mm to about 320 mm. (As noted before, in the embodiments of the present invention, the length and the width of the print image 40 can vary. Specifically, with respect to feminine hygiene articles of the present invention, the length L of the print image 40 can vary from about 10 mm to about 300 mm and the width of the print image 40 can vary from about 5 mm to about 85 mm. However, any desired length and width of the print image 40 can be used in the present invention.)

Referring again to FIG. 11, the first plurality 351 of images 40 is separated from the second plurality 352 of images 40 by an unprinted region B. The unprinted region B represents a portion of the substrate 102 having no print images 40 by the method disclosed herein. (It should be noted that the unprinted region B can include one or more print images, however, the quality of the print image(s) may not be sufficient.) The unprinted region B also represents a portion of the substrate 102 that moved in relation to the printing station 101 (see FIGS. 8 and 9) during the switching between the first and the second print heads 112 and 114, or vice versa. In one embodiment of the present invention, the blank space B is no greater than 50 times the pitch interval P, or no greater than 10 times the pitch interval P, or no greater than 1 time the pitch interval P.

It should be noted that the first plurality 351 of images and/or the second plurality 352 of images could include the same image 40 or different images, wherein the different images, which have been stored in the inkjet controller 211, can be printed on demand at any desired sequence.

Overcoming Limitations of Printing Equipment

Figure 13:
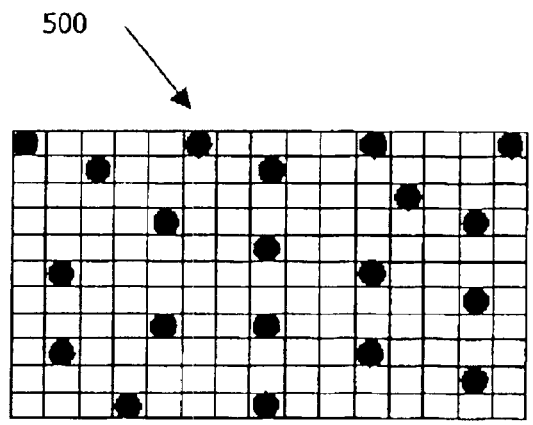
FIG. 13 illustrates a print image having a gray level A at a resolution X-30%.
Figure 14:
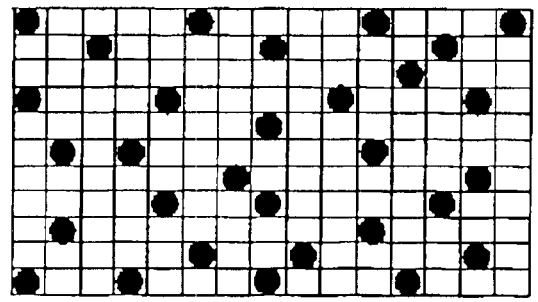
FIG. 14 illustrates a print image having gray level A+30 at a resolution X-30%.

In addition to providing an efficient, uninterrupted operation of two inkjet print heads on a converting line producing hygienic articles, the method of present invention provides an efficient connection between a product designing stage and a product production stage, especially, for the instances having to do with certain limitations of a particular printing equipment utilized for printing inkjet images on the converting line. For example, at high substrate speeds, and, especially, when not one but several ink drops per a dot (i.e., several ink drops, composing a dot, are deposited into a single pixel on the substrate surface) are needed, certain printing equipment may not be capable of printing ink drops at a required rate, resulting in a decreased resolution of the printed image, and, thus, in a decreased visual impression by a consumer viewing the image. The method of the present invention provides compensation for such a decrease of the visual impression by the consumer by adjusting the visual level of the lower resolution image, as shown in FIGS. 12, 13, and 14.

Figure 12:
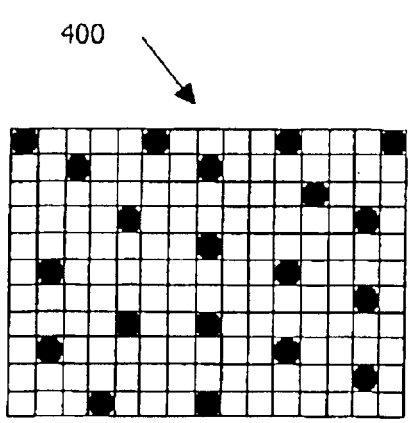
FIG. 12 illustrates a print image having a gray level A at a resolution X.

FIG. 12 shows an inkjet print image 400 having gray level A at resolution X, which, assumingly, for the purpose of explanation, cannot be provided by a given printing equipment at a certain high speed of a substrate. To overcome this speed limitation, the resolution X of the image 400 of FIG. 12 can be stretched, for example, 30% or any other suitable number. FIG. 13 illustrates a print image 500 having the same gray level A as the original image 400 at a lower resolution, X−30%. It can be clearly seen by comparing grids of FIGS. 12 and 13, that the grid of FIG. 13 is longer in one direction in comparison to the grid size in FIG. 12 (in this case about 30%), and, thus, the density of inkjet drops in FIG. 13 is less than the density of drops in FIG. 12, resulting in a less intense visual impression for the consumer. To compensate for the loss of the visual impression, more drops can be deposited in vacant pixels of the stretched grid of FIG. 13, as shown, for example, in FIG. 14, illustrating a print image 600 having a gray level A+30 (which is greater than the original gray level A of the original image 400 of FIG. 12) at a resolution X−30% (which is less than the original resolution X of the original image 400 of FIG. 12). The modified image 600 of FIG. 14 provides a similar visual impression on the consumer as compared to the originally designed image 400 of FIG. 12, thus, overcoming the above described speed limitation of the printing equipment.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inkjet printing in a high efficiency production of hygienic articles, having a print image, on a converting line including at least two inkjet print heads, the method comprising the steps of:
   (a) providing a substrate moving in a web direction at a first velocity;
   (b) printing on the substrate a first plurality of images by a first inkjet print head disposed in proximity to the substrate, the images being separated from each other in the web direction at a pitch interval;
   (c) switching from the first inkjet print head to a second inlet print head while the substrate continues its movement; and
   (d) printing on the substrate a second plurality of images by a second inkjet print head disposed in proximity to the substrate, the images being separated from each other at the pitch interval, wherein the first plurality of images is separated from the second plurality of images by an unprinted region in the web direction, wherein the unprinted region is no greater than 50 times the pitch interval.

2. The method of claim 1, wherein the unprinted region is no greater than 10 times the pitch length.

3. The method of claim 1, wherein the unprinted region is no greater than 1 time the pitch length.

4. The method of claim 1, wherein the step of switching further comprises the steps of:
   a. initiating a second start signal to a converter controller for starting the second inkjet print head;
   b. ceasing sending a first output signal from the converter controller to the inkjet controller; and
   c. sending a second output signal from the converter controller to the inkjet controller.

5. The method of claim 1, wherein the step of switching further comprises the steps of:
   a. ceasing sending a first OK signal from the inkjet controller responding to a fail mode of the first inkjet print head;
   b. ceasing sending a first output signal from the converter controller to the inkjet controller; and
   c. starting sending a second output signal from the converter controller to the inkjet controller.

6. The method of claim 1, wherein the first velocity of the moving substrate is at least 2 meters/second, at least 3 meters/second, at least 4 meters/second, at least 5 meters/second, or at least 6 meters/second.

7. The method of claim 1, wherein the first inkjet print head or the second inkjet print head prints at least 600 images/minute.

8. The method of claim 1, wherein the substrate is a film, a non-woven material, a woven material, a foam material, or any combination thereof.

9. The method of claim 1, wherein the substrate is part of a topsheet, a secondary topsheet, an insert, a backsheet, an absorbent core, or any combination thereof.

10. The method of claim 1, wherein the hygienic articles are feminine hygiene articles, baby diapers, baby pull-on articles, baby swim articles, adult incontinence articles, and dining bibs.

* * * * *